United States Patent
Passivaara et al.

(10) Patent No.: US 6,908,488 B2
(45) Date of Patent: Jun. 21, 2005

(54) SUPPORT DEVICE REPLACING THE EXISTENCE OR FUNCTION OF A LIMB

(75) Inventors: Esa-Pekka Passivaara, Helsinki (FI); Veli-Matti Lempinen, Vantaa Helsinki (FI)

(73) Assignee: Respecta Oy, Helsinki (FI)

( * ) Notice: Subject to any disclaimer, the term of this patent is extended or adjusted under 35 U.S.C. 154(b) by 0 days.

(21) Appl. No.: 10/148,384

(22) PCT Filed: Dec. 18, 2000

(86) PCT No.: PCT/FI00/01105

§ 371 (c)(1),
(2), (4) Date: Sep. 4, 2002

(87) PCT Pub. No.: WO01/43669

PCT Pub. Date: Jun. 21, 2001

(65) Prior Publication Data
US 2003/0125814 A1 Jul. 3, 2003

(30) Foreign Application Priority Data

Dec. 17, 1999 (FI) .............................................. 19992712

(51) Int. Cl.$^7$ .............................. A61F 2/64; A61F 2/70; A61F 5/052
(52) U.S. Cl. ............................. 623/24; 623/44; 602/16
(58) Field of Search ....................... 623/24, 44; 602/16; 601/5

(56) References Cited

U.S. PATENT DOCUMENTS

| | | | | |
|---|---|---|---|---|
| RE22,903 E | * | 8/1947 | Hinkle | .......................... 623/38 |
| 3,683,423 A | * | 8/1972 | Crapanzano | .................. 623/24 |
| 4,263,656 A | * | 4/1981 | Yamaguchi et al. | ........ 702/153 |
| 4,685,926 A | | 8/1987 | Haupt | |
| 4,685,927 A | | 8/1987 | Haupt | |
| 4,997,449 A | | 3/1991 | Prahl et al. | |
| 5,062,856 A | | 11/1991 | Sawamura et al. | |
| 5,344,446 A | | 9/1994 | Sawamura et al. | |
| 5,383,939 A | | 1/1995 | James | |
| 5,840,047 A | | 11/1998 | Stedham | |
| 6,423,098 B1 | * | 7/2002 | Biedermann | .................. 623/24 |

FOREIGN PATENT DOCUMENTS

| | | | |
|---|---|---|---|
| DE | 3923056 | 1/1991 | |
| DE | 4213500 | 10/1993 | |
| EP | 0205785 | 12/1986 | |
| EP | 0209637 | 1/1987 | |
| EP | 0353336 | 2/1990 | |
| EP | 0 549 855 | 7/1993 | |
| EP | 0 628 296 A3 | 12/1994 | |
| GB | 2161386 | 1/1986 | |
| GB | 2 201 260 A * | 8/1988 | ............. A61F/2/70 |
| GB | 2244006 | 11/1991 | |
| WO | WO 91/15170 | 10/1991 | |
| WO | WO 99/00075 | 1/1999 | |
| WO | WO 99/29272 * | 6/1999 | ............. A61F/2/68 |

* cited by examiner

Primary Examiner—David H. Willse
(74) Attorney, Agent, or Firm—Louis Woo

(57) ABSTRACT

A prosthesis or orthosis (orthotic brace) includes at least two parts connected to each other by an artificial joint and a control device to brake or lock the joint. The prosthesis or orthosis includes a sensor which detects the position in relation to a fixed line of a part connected to the joint and which is connected to a control device arranged to influence the joint on the basis of position data given by the sensor. The prosthesis or orthosis is a lower limb prosthesis, such as a thigh prosthesis or a hip ex-articulation prosthesis, or a lower limb orthosis. The sensor is arranged to detect the position of the thigh part in relation to a vertical line. The control device is arranged to influence the movement resistance properties of the joint on the basis of data given by the sensor. The sensor is based on detecting the direction of earth's gravity.

9 Claims, 2 Drawing Sheets

SUPPORT DEVICE REPLACING THE EXISTENCE OR FUNCTION OF A LIMB

Figure 1:
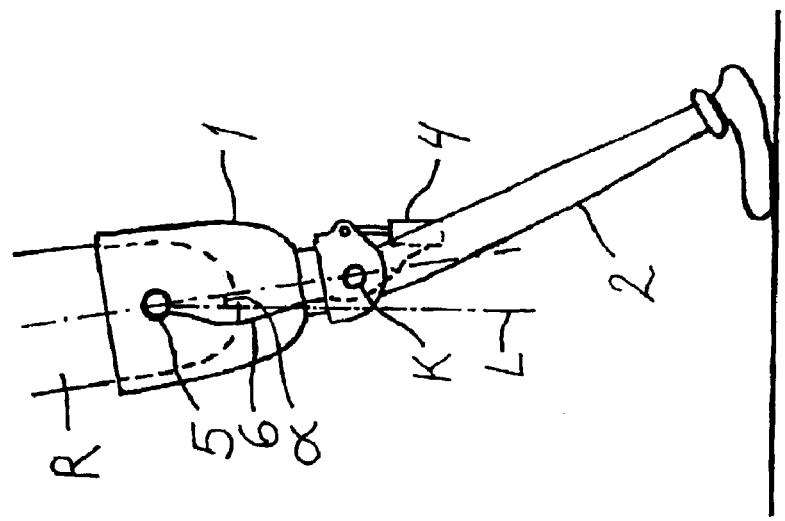

The invention relates to a support device replacing the existence or function of a limb, for example, a prosthesis, comprising at least two parts connected to each other by means of an artificial joint and a control device for the joint. In particular, the invention relates to a lower limb prosthesis comprising an artificial knee joint and a control device for the knee joint.

Said lower limb prosthesis is typically a thigh prosthesis (above-knee prosthesis), and it comprises a foot part which comes against the ground, a shin part, and a thigh part connected to the shin part by means of an artificial knee joint. The thigh part is intended to be connected to an above-knee amputation location, i.e. a thigh stump. Lower limb prostheses also include a hip ex-articulation prosthesis, comprising an artificial hip joint in addition to the artificial knee joint. The invention also includes lower limb orthoses (orthotic braces).

The aim of prior art thigh prostheses is to imitate the movements of a real lower limb as far as possible. To imitate the motor coordination of the human lower limb, different motion detection methods and particularly structures for an artificial knee joint have been developed. Solutions related to the mechanics of a lower limb prosthesis, e.g. relating to the control of the locking force of the knee joint or the locking and release of the joint, are disclosed in European patent 549855, German application publication DE 3923056, British application publication 2161386, and European application publications 205785, 209637 and 353336. A good example of a purely mechanical solution, in which the direction of the load exerted on the knee joint determines whether the knee joint is locked or whether it is free, is the solution presented in international application publication WO 91/15170 (corresponding to U.S. Pat. No. 5,314,498).

The use of sensors is known in connection with neuroprostheses. Neuroprostheses are intended to replace functions of the nervous system and to control the movements of real muscles on the basis of data given by kinetic sensors, and they are thus not prostheses replacing actual moving members of the body, such as lower limbs. Sensor solutions used in connection with neuroprostheses are disclosed e.g. in German application publications 3932405 and 4213500.

An example of a sensor arrangement used in connection with an actual lower limb prosthesis is given in British application publication 2201260. Here, angle sensors are placed at joints of the real leg to measure joint angles, of which information is transmitted to a computer which is, e.g., portable on the back and controls the movements of the lower limb prosthesis according to the postures of the parallel leg. Consequently, this relates to synchronizing the movements of the prosthetic leg with the movements of the functioning leg. This device requires that sensors are attached to appropriate locations in the functioning leg, which impairs comfortable use. Furthermore, the sensors must be connected to a small portable computer which must also be fixed to the body.

The aim of the invention is to present a new device replacing or supporting a body limb. Such a device can be a prosthesis, for example a lower limb prosthesis, which has a simple idea and is easy to implement and which does not require complex sensor systems. The device can also be a so-called orthosis (orthotic brace) provided with an artificial joint to support a limb which is incapable of movement. To achieve this aim, the device according to the invention is primarily characterized in that it comprises a sensor which detects the position in relation to a fixed line of a part connected to the joint and which is coupled to a control device arranged to control the joint on the basis of position data given by the sensor. Such a sensor can be placed e.g. in a part above the knee joint, the thigh part, or a thigh stump connected to it, or that half of the knee joint which pivots together with the thigh part, and it can be an inclination sensor which measures the angle in relation to the vertical position and which is coupled to the control device for the knee joint to control the knee joint on the basis of angular data from the sensor.

The invention is based on the idea that, in fact, the position of the thigh already tells very much about the phase where a step to be taken with the prosthesis leg is. Similarly, the movements of the thigh stump are, due to inherent human coordination of walking movements, naturally correctly synchronized with the movements of the parallel functioning leg. Because of this, it is, in fact, not absolutely necessary to know the position of the functioning leg for controlling the function of the prosthesis.

The device for controlling the knee joint is, in its simplest form, a locking or braking device. In this case, it is arranged, at certain angular readings given by the sensor, to lock/brake the knee joint and, at certain readings, in turn, to release the locking or to reduce the braking force of the knee joint. As the device for controlling the knee joints, it is possible to use many types of devices which will be discussed below.

The sensor detects the angle to a fixed line, i.e. the absolute angle. The sensor is preferably based on the effect of gravitational force; that is, the sensor used can be an inclinometer known in the respective field, which can be used to measure the inclination of objects or parts in relation to a vertical line, i.e. a line parallel to earth's gravity. Consequently, in practice, the sensor measures the inclination of the thigh, which indicates the phase of a step taken with the prosthetic leg very accurately.

The sensor can be placed in the thigh part of the device itself, but it can also be attached to the thigh stump or be placed in that half of the knee joint to which the thigh part is connected. The main idea is that the sensor is capable of monitoring the position of the thigh stump or the thigh part of the device, and it can quickly transmit a message to the device for controlling the knee joint. Thanks to the sensor, the operation of the device can be adjusted according to the individual needs of the user.

According to one embodiment, also the second part connected to the joint comprises a sensor operating in a corresponding manner, to give more information about the position of the device.

Figure 2:
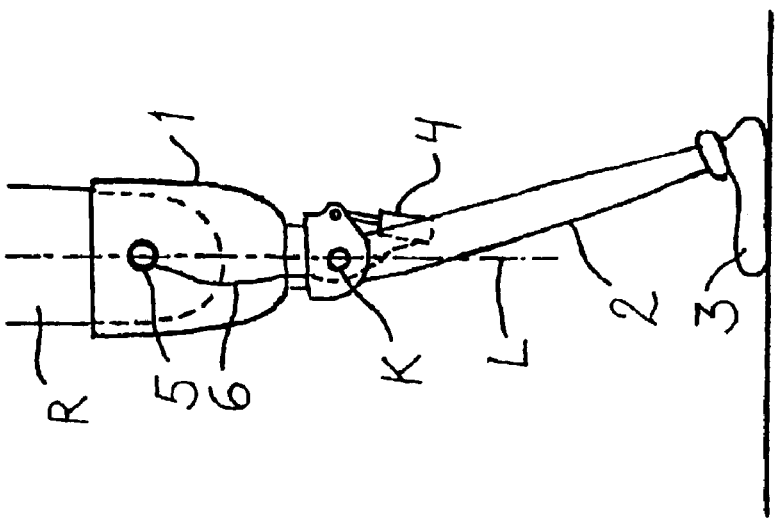
Figure 3:
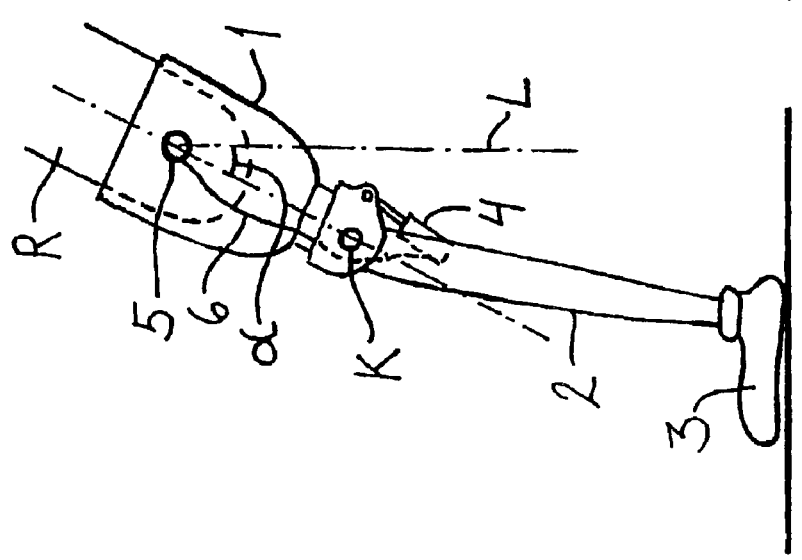
Figure 4:
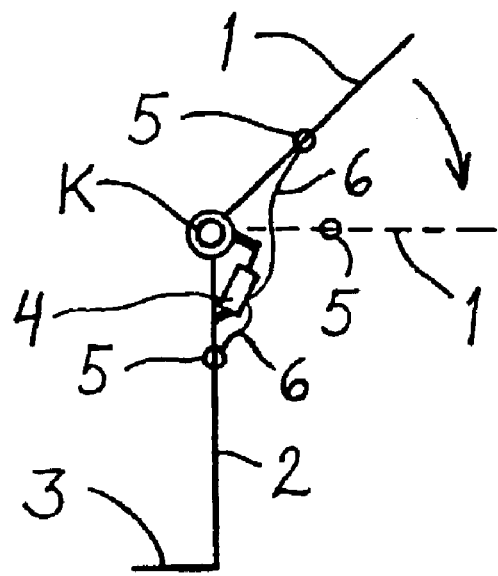
Figure 5:
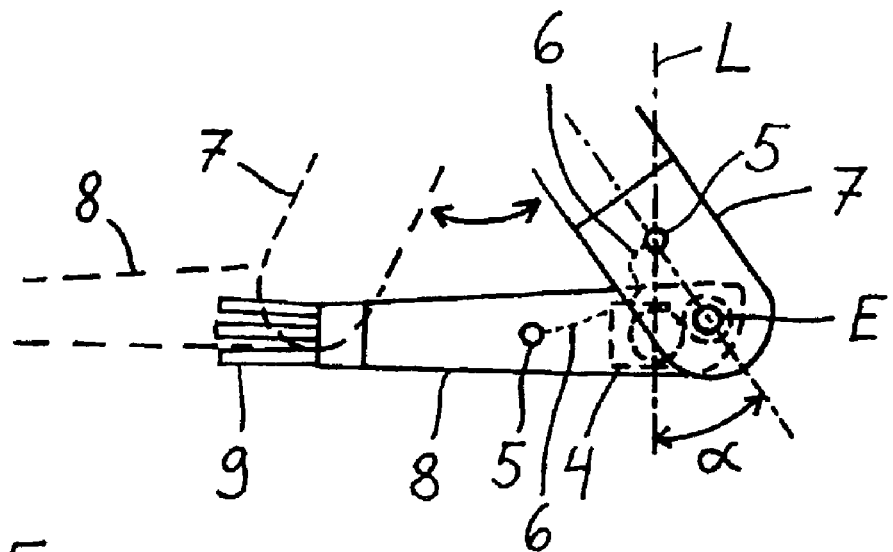

In the following, the invention will be described in more detail with reference to the appended drawings, in which FIG. 1 shows a lower limb prosthesis and its operation in the first phase of a step, FIG. 2 shows the same in the second phase of the step, FIG. 3 shows the same in the third phase of the step, FIG. 4 shows an embodiment with two sensors, and FIG. 5 shows an upper limb prosthesis and its operation.

FIG. 1 shows a side view of a prosthesis according to the invention, fixed to a thigh stump. The prosthesis comprises a thigh part 1 which is fixed by suitable appliances to a thigh stump R and is provided with a fitting part for the fixing, for example a socket with a known structure, a shin part 2 pivotally connected to the thigh part by means of a knee joint K, and a foot part 3 connected to the lower end of the shin part. In the movements of the shin part 2 and the foot part 3, the aim is to imitate the movements of an ankle, and here it is possible to use bio-mechanical solutions known from mechanical solutions of prostheses. Similarly, for the mechanical solutions of the knee joint, reference is made to methods generally known in the field to articulate the thigh part and the shin part with each other.

The movement and the resistance to movement between the thigh part 1 and the shin part 2, and the change in the angle therebetween, i.e. the angle of the knee joint K, are controlled with a knee joint control device 4. In the case shown in the figure, this control device 4 is a hydraulic pump whose length is variable and which allows the flexion of the joint K, brakes it or locks it completely. The pump is connected at its opposite ends to the pivotal parts of the joint, wherein its length is changed according to the flexion of the joint; that is, the cylinder part is connected to the first pivotable half and the piston rod to the second pivotable half. The operating principle can be such that in the cylinder of the pump, the chambers on opposite sides of the piston are coupled to each other by means of a hydraulic fluid line provided with a valve for adjusting the flow and for simultaneously adjusting the resistance to movement caused by the pump, for example a magnetic valve. Thus, the pump is used as a device for attenuating the movement and not for actively moving the knee.

The figures show how a valve 5, which is capable of measuring the position of the thigh and the thigh part 1 in relation to the direction of earth's gravity, is placed in the thigh part 1, for example on the side of the fitting part which receives the thigh stump R. The sensor can thus indicate, for example, the inclination of the straight line between the hip joint and the artificial knee joint K, the "longitudinal axis of the thigh", in relation to the vertical line. The sensor 5 gives an electrical control message along a data communication line 6 to the knee joint control device 4, for example to a magnetic valve of the hydraulic pump. The data given by the sensor is processed is in a processor which gives the actual control command to the knee joint control device 4.

FIGS. 1 to 3 show, primarily for illustrative purposes, the sensor 5 located far from the knee joint. According to a more preferable alternative, the sensor 5 is in that part of the knee joint which pivots together with the thigh part 1. In this position, the sensor can be close to the control device 4, and the line 6 to the control device is short.

When a step is being taken with the prosthetic leg, the user must be sure that the knee joint K is stiff. FIG. 1 shows a situation in which the prosthesis leg is about to step down to the ground, that is, according to the motor coordination, the thigh and the thigh part 1 of the prosthesis are inclined as far as possible forward and the foot part 3 hits the ground. The prosthesis user's centre of gravity is thus on the rear side of the knee joint K, and the knee joint is stiffened by means of the control device 4. For the control automatics of the knee joint, e.g. a processor, it is possible to determine the values of the angle $\alpha$ between the longitudinal axis of the thigh and the vertical line L (parallel to earth's gravity), i.e. a certain angular range in which the knee joint K is made stiff.

FIG. 2 shows a situation in which the whole weight is carried by the prosthetic leg. The user's centre of gravity is approximately above the knee joint K. In this situation, the thigh is in vertical position, i.e. the angle $\alpha$ to the vertical line L is 0. Also in this situation, the knee joint K is still kept locked.

FIG. 3 shows a situation in which the longitudinal axis of the thigh is inclined backwards; in other words, if the angle $\alpha$ of inclination forward is taken to be positive, in this situation the angle $\alpha$ is negative, i.e., the longitudinal axis of the thigh is behind the vertical line L in the walking direction. When the angular value given by the sensor 5 has decreased below a certain limit while the thigh part 1 was inclined backwards, the centre of gravity has moved to the front of the knee joint K and the processor gives the control device 4 a command to release the locking of the knee joint. The knee joint is now capable of flexing according to natural gait. When the prosthetic leg is swung forward during a new step, it is straightened, and after the angle $\alpha$ has exceeded said value, the knee joint is locked again before the foot hits the ground.

The knee joint K comprises, in addition to a hydraulic pump and a magnetic valve for its control, a processor and a power supply required by the electronics, such as a battery, and, as was mentioned above, the sensor 5 can also be placed in the knee joint, in that pivotable half to which the thigh part 1 with its fitting part is connected.

The whole prosthesis is ready for use as soon as it has been fixed to the thigh stump by means of a suitable fixing arrangement. The requirement is that the sensor 5 is placed in such a location in the prosthesis where it detects the position of the thigh part 1 and thereby the thigh stump R as precisely as possible by means of the earth's gravity. Thus, the invention can also include an alternative, in which the sensor 5 is attached to the thigh stump R itself, and it is connected to the control device 4 by means of the data communication line 6.

The knee joint can be locked by increasing the flow resistance to the flow between the ends of the hydraulic pump by closing the valve, and it can be released by reducing the flow resistance by opening the valve. It is not necessary to cut off the flow completely, if the pump is otherwise sufficiently stiff. Preferably, the valve can be adjusted in such a way that the resistance to movement of the joint in locked state and in released state can be adjusted.

According to an advantageous alternative, the limits for the movements can also be reset; that is, the limit value of the angle $\alpha$ at which the control device 4 changes the state of the joint K can be changed according to individual requirements. This can be performed, for example, by entering new data in the processor of the control device 4 or by turning the sensor 5 in such a way that its scale and the respective angular limit value are changed.

It is also possible to use different angular limit values depending on whether the prosthesis leg is going to move forward or backward. In this case, for data processing, the processor must also know the direction of change of the angle $\alpha$.

The invention can also be applied in hip ex-articulation prostheses, in which the prosthetics part 1 corresponds to the whole thigh. The sensor 5 can be connected to such a thigh part, for example, a so-called thigh tube, and it can control the artificial knee joint K as described above. The invention can be generally applied in all support devices comprising two arms connected to each other by means of a joint and intended to replace the existence or function of a corresponding limb in the body. Consequently, the invention also includes orthoses (orthotic braces), for example of the type comprising an artificial knee joint to replace a knee unable to move, with parts to be fixed to the thigh and to the shin on its both sides. The function of the control means 4 on the basis of angular values given by the sensor 5 of the thigh part 1 can be implemented in a way analogical with the above description.

Instead of a passive control device with a variable resistance, the knee joint K can have an active control device which is effective between the parts and produces their movement around the point of articulation.

Using such an e.g. electrically actuated device, it is possible to achieve a locking action (the actuator stopped and the movement locked) and releasing action (actuator free) but also an active movement (transmission of motion force from the actuator). Such a device can also be arranged to resist a movement with a certain force. By means of an active control device, it is possible, for example, to implement the flexion of the knee to a predetermined angle when the support device (prosthesis or orthosis) is in the rear position, and the extension of the knee when the support device is moved forward, on the basis of position data indicated by the sensor 5 at each time.

FIG. 4 shows schematically an idea, according to which also the second part pivotable in relation to the knee joint K, the shin part 2, is provided with a sensor 5 functioning in the same way as the sensor of the thigh part, detecting the angle of inclination of the part compared to the fixed line L. Also this sensor 5 is based on detecting the direction of earth's gravity. The data given by both sensors 5 can be processed in the processor of the support device to provide overall data on the position of the support device. For example, when sitting down, the knee joint K is kept released or the motion resistance caused by the control device 4 is kept such that sitting down is possible, even though the sensor 5 on the side of the thigh part 1 detects the forward movement of the thigh (the angle α increases), during which movement the joint should be locked. It is possible to keep the knee joint released, because the sensor 5 on the side of the shin part detects that the longitudinal axis of the shin part 2 is within an angular range determined for the sitting down movement. When the support device leg is in extended state, the knee joint K is locked. Before sitting down, the knee joint K is released by a special function (e.g. manually by a control means, such as a press button, attached to the body or to the support device). In a corresponding manner, when standing up, it is possible to use the healthy leg and an arm/the arms as a support, or if the knee joint K comprises an active control device, it can be used as a help during standing up. The knee joint K is kept released, until the sensor 5 on the side of the thigh part 1 indicates that the angle α has decreased to a predetermined limit value, or until the angle between the thigh part and the shin part (joint angle) has, after the extension of the support device leg, increased to a predetermined value which can be observed by combining the data from both of the sensors 5.

Also the second sensor 5 can be placed at any location on the shin part side of the knee joint K. The sensor 5 can be in any part pivotable together with the movement of the shin part. The sensor 5 can be close to the control device 4, in which position the line 6 to the control device is short. The sensors 5 detecting the angle of inclination of the part in relation to the fixed line by means of earth's gravity are advantageous also in the sense that they can be placed in the most appropriate location in the pivotal part to lie separate from the actual joint structure, and no measurement of the joint angle needs to be arranged in the joint.

The invention can also be applied in a support device replacing the existence or function of an upper limb. FIG. 5 shows an upper arm part 7 attached to the body (for example to the stump of an upper arm) and provided with a sensor 5 which is capable of measuring the position of the upper arm and the upper arm part 7 in relation to earth's gravity, i.e. the inclination a in relation to a fixed vertical line L. The upper arm part pivots together with the movement of the stump of the upper arm. For example, when the upper arm part is moved forward from a predetermined position (extension of the arm), in which a forearm part 8 lying on the other side of an artificial elbow joint E and pivotable in relation to the upper arm part, is horizontal or at a predetermined angle in relation to the horizontal plane, said latter position being detectable with a corresponding sensor 5 in this part 8, it is possible, by means of angular data from the sensor 5 of the upper arm part 7 and the processor, to control the rotation of the joint by the active control device 4 of the elbow joint E in such a way that the forearm part 8 retains its direction or the motion path of the hand part 9 at its end is straight. Control commands to the active control device 4, e.g. an electrically operated actuator, can be given by suitable movements of the upper part of the body. The same ideas can also be applied in an upper limb orthosis, connected to the arm unable to move and provided with an artificial elbow joint to be rotated by an active actuator.

What is claimed is:

1. A prosthetic or orthotic support device for replacing the existence or function of a limb of a body, comprising:
   a first part and a second part connected to each other by an artificial knee joint including a pivot, of which parts the first part is a thigh part, which is configured to be fixed to a person's body or which is a part positioned to be closer to the body than the second part, seen from the artificial knee joint;
   a control device for the artificial joint, and
   a sensor arranged to detect the inclinational position in relation to a fixed line of said thigh part and placed on that side of the pivot of the artificial knee joint which is pivotable together with the movement of the thigh part;
   said sensor being coupled to the control device, which is arranged to influence movement resistance properties of the artificial knee joint on the basis of data about said inclinational position given by said sensor in a predetermined inclinational position of said thigh part.

2. The support device according to claim 1, wherein in a first inclinational position of the part, the control device is arranged to brake the artificial knee joint or to lock the artificial knee joint, and in a second position, the control device is arranged to release the locking of the artificial knee joint or to relieve the braking.

3. The support device according to claim 2, wherein the first position comprises a first range of angles of inclination and the second position comprises a second range of angles of inclination, wherein a predetermined limit value between the first range and the second range is determined for the sensor or the control device, at which limit value the control device is arranged to change the movement resistance properties of the artificial knee joint.

4. The support device according to claim 3, wherein the control device is arranged, on the basis of the inclinational position data given by the sensor, to release the locking of the artificial knee joint or to relieve its braking when the thigh part of the support device moves backward from a forwardly inclined position, and to lock the joint or to increase its braking when the thigh part of the support device moves forward from a backwardly inclined position.

5. The support device according to claim 3, wherein the limit value can be changed in the support device.

6. The support device according to claim 1, wherein the control device is a pump which is used as an attenuator between the pivotal halves of the artificial knee joint and which has an adjustable resistance to the flow of the medium.

7. The support device according to claim 1, wherein, to determine the position of both parts connected to each other by means of the artificial knee joint, the support device also comprises a second sensor which is arranged to detect the position of the second part connected to the artificial knee joint.

8. The support device according to claim 1, wherein the sensor is a sensor detecting along the direction of earth's gravity.

9. The support device according to claim 1, wherein said part fixable to the body or closer to the body is a part movable by means of the body.

* * * * *